(12) United States Patent
Hoffman

(10) Patent No.: US 6,506,052 B1
(45) Date of Patent: Jan. 14, 2003

(54) CONVERSION SYSTEM FOR NON-IMPLANT ANCHORED DENTURES

(76) Inventor: Larry I. Hoffman, 770 Sumac, Highland Park, IL (US) 60035

(*) Notice: Subject to any disclaimer, the term of this patent is extended or adjusted under 35 U.S.C. 154(b) by 0 days.

(21) Appl. No.: 09/525,960

(22) Filed: Mar. 15, 2000

(51) Int. Cl.[7] .............................................. A61C 13/12
(52) U.S. Cl. ....................................................... 433/181
(58) Field of Search ................................. 433/171, 180, 433/181, 182, 172, 173

(56) References Cited

U.S. PATENT DOCUMENTS

| | | | | |
|---|---|---|---|---|
| 4,290,755 A | * | 9/1981 | Scott | 433/173 |
| 4,787,851 A | * | 11/1988 | Kusano et al. | 433/173 |
| 4,808,110 A | * | 2/1989 | Rametti | 433/172 |
| 5,427,906 A | * | 6/1995 | Hansen | 433/173 |
| 5,678,997 A | * | 10/1997 | De Buck | 433/177 |

* cited by examiner

Primary Examiner—Todd E. Manahan
(74) Attorney, Agent, or Firm—John D. Long

(57) ABSTRACT

A system of retrofitting non-dental implant secured dentures with dental implant technology in order to save time and expenses to the denture wearer and to provide a marketing capability that uses the benefits of retrofitted dentures as communicated to denture wearers to convince the denture wearers to receive dental implants.

The retrofitting of the said denture comprises of modifying the depression receptacle of the denture base to accept a portion of the exposed part of at least one implant affixed to the denture wearer and to accept a portion of the dental implant securing device. A portion of the dental implant securing device is affixed to the depression receptacle so as to positioned dental implant securing device to reversible attach to at least a portion of the exposed art of at least one implant affixed to the denture wearer when the denture is affixed to the denture wearer.

9 Claims, 5 Drawing Sheets

CONVERSION SYSTEM FOR NON-IMPLANT ANCHORED DENTURES

CROSS-REFERENCES TO RELATED PATENTS

Not Applicable

STATEMENT REGARDING FEDERALLY SPONSORED RESEARCH OR DEVELOPEMENT

Not Applicable

REFERENCE TO A "MICROFICHE APPENDIX"

Not Applicable

BACKGROUND OF THE INVENTION

A) Field of the Invention

This invention pertains in general to dental systems that are used to replace teeth that are lost due to age, accident, diseases or other reasons. In particular, the invention pertains to the conversion of a non-implant anchored denture prosthesis to be compatible with dental implant fitted to a denture wearer. This invention also pertains to the marketing of dental implants to denture wearer through the communication of the benefits of this retrofitting system.

B) Background of the Invention

The loss of teeth can lead to speech and eating impairment, with the significant tooth loss considered a social stigma in a culture which places an emphasis on and considers to be a thing of beauty, a smile with a full set of white teeth. As result, the dental profession for centuries has worked to develop dental systems that replaces lost teeth of its patients with a prosthesis which takes up the functions (eating and aiding in talking) as well as the actual appearance of the lost teeth.

The tireless efforts of the dental profession have given rise to three well-accepted systems for of tooth replacement. Two of these systems, the dentures (removable prosthesis) system and the bridges (non-removable prosthesis) system, have been in use for a long time. These systems are similar that they both utilize tooth replacement prosthesis to addresses only the replacement of a part of the missing tooth, namely the exposed portion of the tooth known as the crown.

The denture is a removable dental prosthesis which has artificial teeth imbedded in a denture base resembling the gum or gingiva. The denture base provides the support for the prosthesis by resting on the gingiva. The underside of the denture base has a depression receptacle that receives at least a portion of the gingiva so as to provide a snug, reversible fit of the denture onto the gingiva that was adjacent to the lost teeth.

The denture could either be a partial denture in only replacing a few teeth or it could full denture in replacing an entire set of teeth. A full denture would replace the lower set of teeth ("lower denture") or upper set of teeth ("upper denture"). With the full denture, the surface of the depression receptacle base adheres to the appropriate gingiva of the denture wearer through saliva from the wearer's mouth causing a vacuum between the surface of the depression receptacle and the mucus membranes of the gingiva. In the case of partial dentures, these dentures traditionally reversibly secure to the gingiva through the use of specially design adhesive that is applied to the gingiva and the depression receptacle for that purpose.

A bridge prosthesis is similar to that of a denture prosthesis except the bridge is normally a limited to being partial denture which is non-reversibly cemented or otherwise affixed to the adjacent teeth.

The third and latest system for tooth loss replacement is the system of dental implants otherwise known as the field of dental implantology. This field addresses the loss of the entire tooth including the root which is the anchoring and weight bearing structure for the tooth.

Dental implantology embeds an artificial implant into jawbone of the patient to replace or supplant the root of the patient's missing tooth. These implants can come in a wide variety of shapes, sizes, designs and compositions. The implant can have an attachment or cap placed on its exposed portion that protrudes through the gingiva to facilitate the non-reversible fitting of the artificial crown on the top of the implant. If there is additional tooth loss, multiple implant-artificial crowns can be used to replace the lost teeth.

Sometimes to be cost effective or if the patient's dental condition requires its or both, the dental profession combines the denture system with dental implantology so to create a dentures that are reversibly secured to a patient by a dental implant system. This system can be used to reversibly secure partial or full dentures. In this type of tooth loss replacement system, the dental implant is first applied to the patient. In general, the denture, especially a full denture, requires the placement of one or more dental implants into patient to form the basis for reversibly affixing the denture to the patient.

After the implants have been properly affixed to jaw bone of the patient, a new denture is then constructed to fit in with the remaining teeth, if any. The depression receptacle of the denture is made to receive the patient's gingiva, the exposed portions of the dental implant(s) and at least one securing device that allows the denture to reversibly attached to the exposed portion of the implant(s).

The type of securing device selected depends on the type of implant used. Commonly, the securing device can be a resilient C-clip or saddle clip that straddles a post that is horizontally mounted between two post-type implants. The securing device can also be a female receptacle containing an elastomeric O-ring retainer that reversible affixes to a cap affixed to the exposed potion of the implant. The cap is male with an external grove that reversibly accommodates the O-ring set into the female receptacle. The securing device is affixed to the denture by adhesive to the space created for it in the denture base.

In this manner, the denture can be more efficiently, reliably and securely attached to the patient than through the use of attachment systems such as saliva-vacuum or adhesive. The use of implant system which incorporates stand-alone anchor and weight bearing supports, has help to alleviated a lot of the problems associated with the earlier tooth replacement systems (removable dentures which causing embarrassment to the patient when unexpectantly falling out of place, fixed bridges adding stress adjacent teeth by relying on them for support).

However, since it is standard dental practice at present when installing in a patient an dental implant system using dentures, is to make a new denture that was specifically deigned and made to be reversibly attach to the patient's dental implants. Usually this manufacture of new dentures takes two or three dental visits spread over a long period of time.

As such, the present dental implant system fails to address the situation of the denture wearer who already has dentures (non-dental implant attached type). The current system requires the denture wearer to acquire a second set of dentures and to expend considerable cost and time to have these implant-specific dentures made.

This is especially true for denture wearers, who as they get older, either through the aging process or advancement of dental disease, experience a change in their gingiva or jaw bone mass. This mass losses or shape change would prevent the gingiva from closely engaging the denture base preventing the normal saliva-vacuum attachment system from being a fully effective denture securing means.

Further, a significant number of the denture wearers, even with the rising prominence of field of dental implantology, are accustom to and only understand systems and science (dentures and bridges) that have existed for a long time. These denture wearers sometimes lack the necessary understanding of dental implantology to fully appreciate the benefits that can be afforded to them by this newer system.

As a result of these current dental implant protocols, the denture wear even when grasping the understanding of the benefits of dental implant technology must under go the additional time and significant expenses of associated with making and fitting new dentures to replace their old non-implant based dentures.

BRIEF SUMMARY OF THE INVENTION

It is the primary object of this invention to provide a system that modifies non-implant secured dentures by retrofitting the dentures with implant technology to allow the old dentures to be able to reversibly attached to dental implants affixed to the denture wearer. It is also an objective of this system to market the dental implant technology and its benefits to denture wearers by communicating to the denture wearers that their old ill-fitting dentures can be converted to an attachment system which makes their old dentures once again securely and easily attach to the denture wearer.

It is a further objective of this invention to modify the non-dental implant compatible dentures to use replaceable clips that reversibly fasten the dentures to dental implant.

It is further objective of this invention to provide to wearers of non-dental implant dentures a reversible securing mechanism for their dentures to that is superior to the saliva-vacuum grip or the adhesive securing methods that are commonly used by such denature wearers.

It is yet another object of this invention, to help reduce the possibility to wearers of non-dental implant dentures that their dentures would be accidentally dislodged under embarrassing circumstances.

It is a still another objective of the invention to modify an originally non-dental implant secured dentures which no longer closely or securely fit wearer due to aging or advancement disease accept securing apparatus that will allow the improve the securing capabilities of the denture to the denture wearer.

It is yet another objective of the invention to allow the denture wearer who is to receive dental implants without having to incur additional time and the additional expense of making an additional denture that is specifically made for dental implants.

It is yet another object of the invention to modify to originally non-dental implant type dentures to accept a reversible attachment device which is less susceptible to changes in the patient's jaw bone mass or gingiva shape.

DETAILED DESCRIPTION OF THE INVENTION

The inventor does not claim either the dental implant technology or the technology used to make dentures. The invention encompasses the modification of dentures, which were originally constructed to adhere to the denture wearer through non-dental implant securing methods, by retrofitting such dentures with dental implant technology so that said retrofitted dentures could be reversibly attached to at least one dental implant fitted to the denture wearer. The invention further includes an efficient marketing of dental implant technology to denture wearers by communicating to the denture wearers the benefits of retrofitting denture technology to their non-dental implant secured dentures as a means of overcoming the natural reticence of said denture wearers to newer technologies such as dental implantology.

Figure 1:
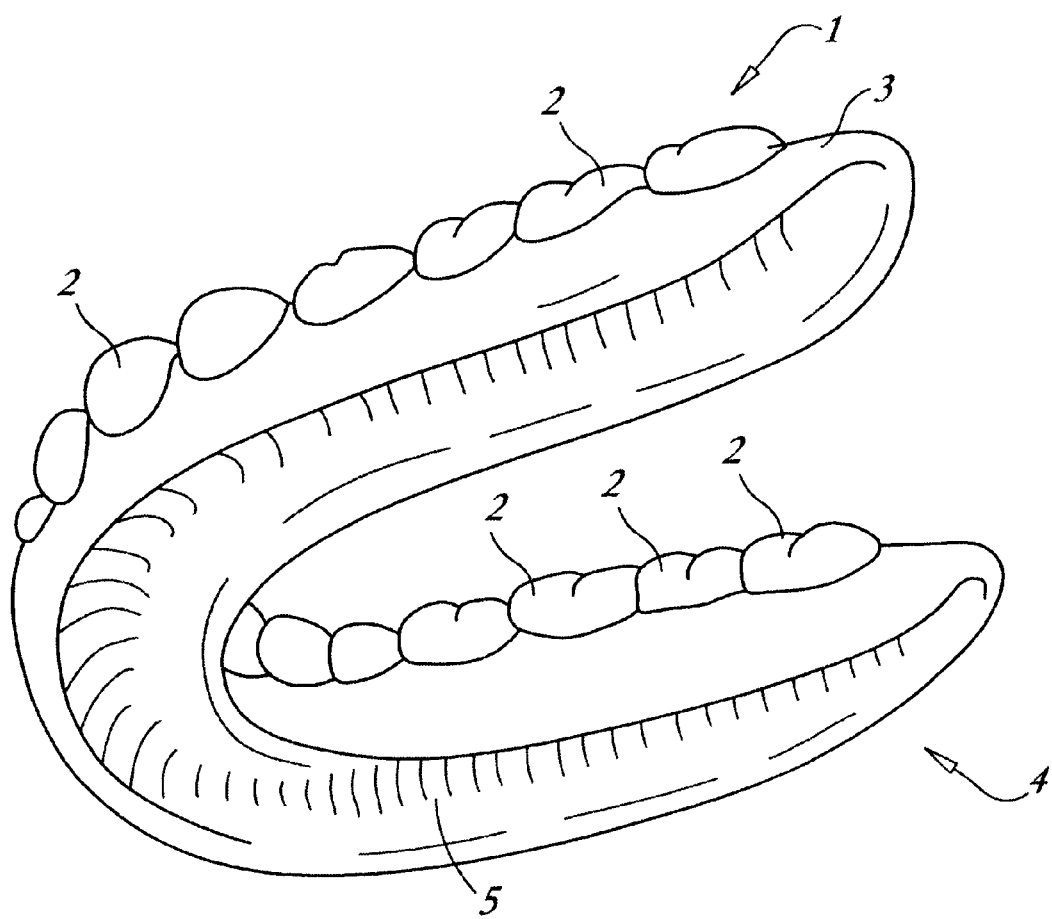
FIG. 1.) A perspective drawing of the invention showing the underside view of a non-dental implant denture.

FIG. 1 shows perspective view of a full plate denture 1 that is of the type typically worn by denture wearers who are not fitted with dental implants which are used to reversibly attach dentures to the denture wearer. The said denture is usually secured to denture wearer through special adhesive, saliva-vacuum attachment or other non-dental implant securing means. Denture which can be retrofitted with implant technology can be a full denture (upper or lower or both) or a partial denture. For the purposes of this disclosure, a lower full denture will be shown as being retrofitted with dental implant technology. It should be understood that the retrofitting methodology as set forth can be applied, using minor changes or modifications easily accomplished by those versed in the art, to a wide variety of dentures types, including but not limited to, upper, lower and partial dentures.

The denture, generally denoted as 1, comprises of false teeth 2 embedded in the denture base 3. The false teeth 2 and denture base 3 are colored and contoured to give the appearance of real teeth and gingiva. The underside 4 or the non-crown side of the denture base 3 has a depression receptacle 5 which was molded or otherwise fitted to match and receive the contours of the denture wearer's gingiva that used to surround the missing teeth. An alternative embodiment of the invention also provides for the retrofitting of a partial denture with dental implant technology to allow the retrofitted partial denture to be reversibly attached to the denture wearer by a dental implant securing apparatus.

Figure 2:
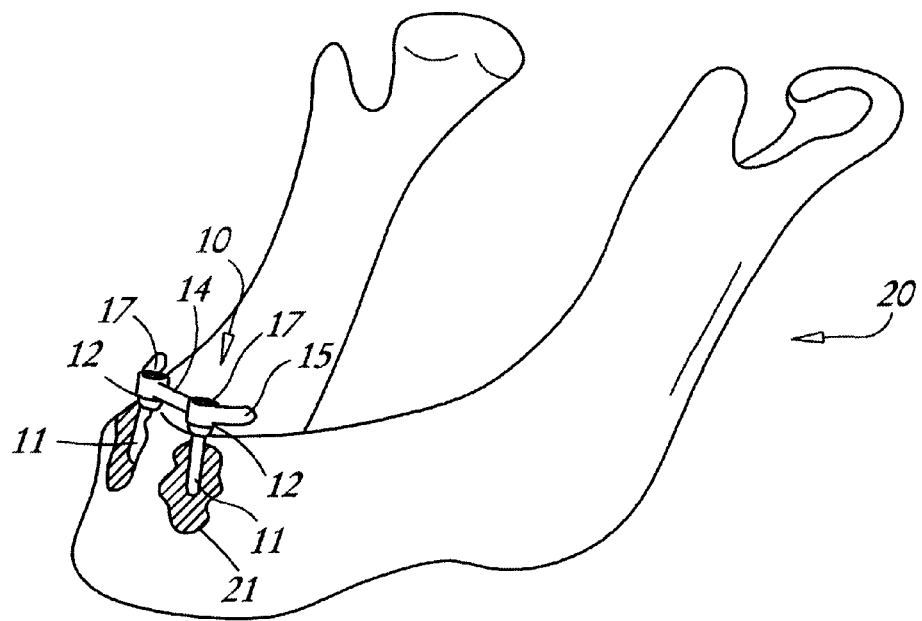
FIG. 2.) A perspective partial cutaway drawing of the invention showing how an implant are placed into the bone of the jaw.

As shown in FIGS. 2, at least one dental implant, generally denoted by 10, using standard dental techniques well known to those versed in the art, is affixed to the denture wearer. The implant 10 is affixed either to the denture wearer's jaw bone 20 for reversibly securing lower (full or partial) dentures or is applied to the denture wear's palate for reversibly securing upper (full or partial) dentures, or to both the jaw bone and the palate if a full set of upper and lower dentures are being retrofitted. The dental implant affixed to the denture wearer to secure the retrofitted denture can be selected from a variety of different dental implant systems, all of which are well known to one versed in the art and are selected on the basis of dental professional's preference, economy, patient condition and other factors.

There are at least three basic types of dental implant systems that can be used to retrofit non-dental implant secured dentures: the cylinder-post implant system, the blade implant system & the subperiosteal implant system. The selection of which system to use on a denture wearer whose denture is being retrofitted depends on the denture wearer's condition, dental professional's preference, expense and other factors. For example, considerations of the denture's wearer's condition include that fact that the cylinder-post implant system and the blade implant systems can only be affixed to denture wearers who have adequate bone (jaw bone/palate) height and thickness to adequately support the implant; that the subperiosteal implant is used whenever the denture wearer's bone (jaw bone/palate) structure has lost significant bone mass which can occur due to such factors as age, dental disease or wearing of dentures.

The three implant systems (cylinder-post, blade and subperiosteal) differ in the type of anchoring device that is applied to the dental wearer's jaw. The cylinder-post implant type, which is implant system that is used in the preferred embodiment, uses a generally pillar-shaped anchor that is embedded in a vertical position in the denture wearer's bone (jaw bone/palate). The blade implant embeds a blade-shaped latticework into the denture wearer's bone (jaw bone/palate) while the subperiosteal implant places a latticework anchor attached over the denture wearer's bone (jaw bone/palate) and under the surrounding gingiva.

All three implant systems use at least an anchor 11, a cap 14 and a securing device generally denoted as 13. The securing device 13 is attached to the denture 1 to reversibly attach the denture to the implant device 10. The anchor 20 is the artificial implant that acts as and supplants the missing tooth's root.

In the preferred embodiment for the retrofitting of a full denture, at least two anchors 11 of the cylinder-post type are surgically imbedded in the denture wearer for the securement of one full denture. The anchors are placed at the anterior portion of the denture wearer's jaw bone 20 (for securing a lower denture) or the palate (for securing an upper denture). Two sets of two anchors are used in for securing a set of upper and lower full dentures in both the jaw bone 20 and palate, one sent for each denture. The set of anchors is placed so that each anchor 11 is apart from one another.

After the anchors 11 are surgically affixed to denture wearer's bone (jaw bone/palate), the bony matter 21 is given time to solidly attach to the base of the anchors 11. After that has occurred, caps 12 are placed on the exposed ends of the anchors 11.

In an alternative embodiment, the caps 12 themselves which directly interface with and attaches to the securing device 13 attached to the denture. The cap 12 forms the male portion of the male-female o-ring snap attachment device which received into the interior of a matching female portion of the male-female O-ring snap attachment device which is retrofitted to the denture 1. In such cases, where a full denture is being used, a series (usually four) of these implants and caps are placed at the anterior portion of the denture wearer's bone (jaw bone/palate) for reversibly connecting to the retrofitted denture.

In the preferred embodiment of the invention, a saddle bar, generally denoted as 14, which is a generally horizontal post attached to the caps 12 affixed to the anchors 11. The saddle bar 14 thus straddles the exposed portions of at least two anchors 11. The saddle bar 14 of preferred embodiment is comprised of three sections: two external wings 15 and a main bar 16. An external wing 15, located at each end of the main bar 16, is gently angled to follow curvature of the jaw line (jaw bone or palate) while still generally maintaining the horizontally axial relationship with the main bar 16. The connection of each external wing 15 with the main bar 16 forms a vertical aperture 17 located between that external wing 15 and the main bar 16. These apertures 17 are sized and located to accept the caps 12 attached to the 11 anchors. The appropriate technique, well known to the practitioner of the art, is then used to secure the saddle bar 14 to the caps 11 giving the exposed portion of the implant 10 a "hitching post" appearance.

Figure 2A:
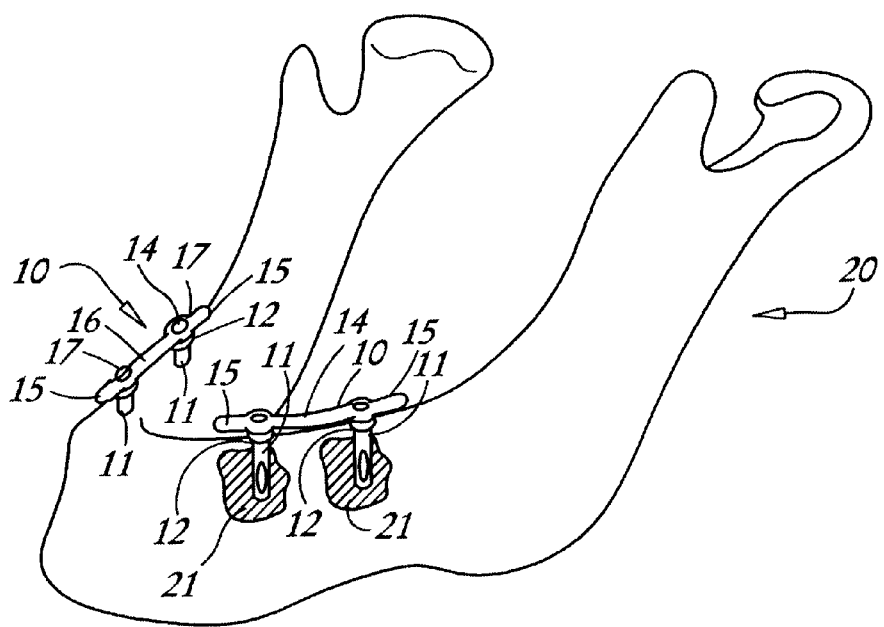
FIG. 2A.) A perspective partial cutaway drawing of the invention showing an alternate embodiment of multiple implants being placed into the bone of the jaw FIG. 3.) A perspective partial cutaway view of the invention showing the depressions created in the underside of the denture to accommodate an exposed portion of the implant.

As shown in FIG. 2A, an alternate embodiment of the invention for full denture uses two separate saddle bar implants anteriorly placed in mirror positions on the anterior portion of the denture wearer's bone (jaw bone/palate) for securing a retrofitted lower denture. As stated above similarly placed implant on the palate would be used for the securing of a retrofitted upper denture.

After the completing the affixation of the dental implants 10 to the denture wearer, standard denture construction techniques, well known to those versed in the art, are employed to modify the denture wearer's non-implant secured denture 1 to accept and be secured by the denture wearer's implant.

Figure 3:
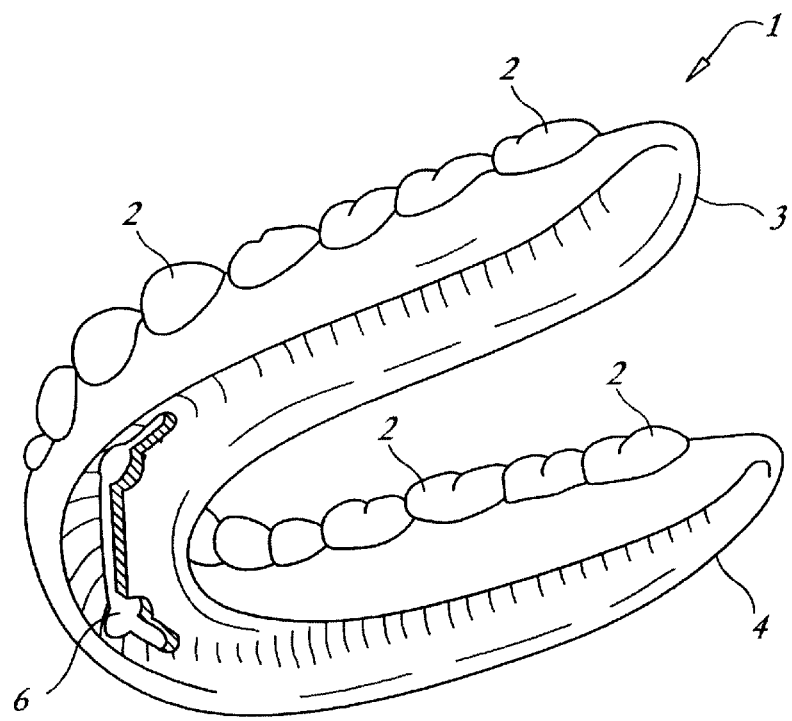
FIG. 3A.) A perspective partial cutaway view of the invention which shows an alternate embodiment where the depressions created in the underside of the denture to accommodate an exposed portions of multiple implants.
Figure 3A:
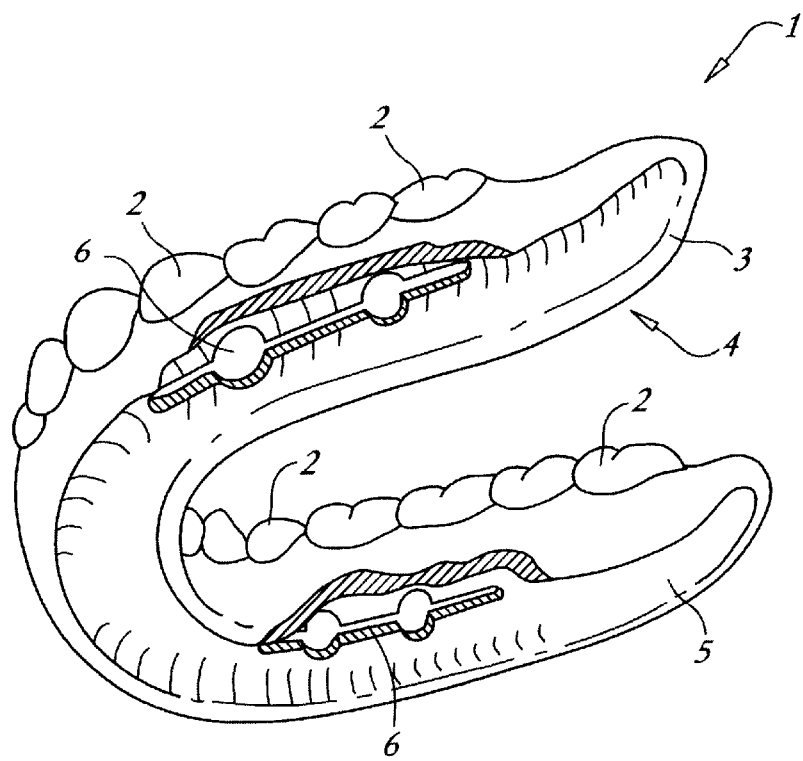
Figure 4:
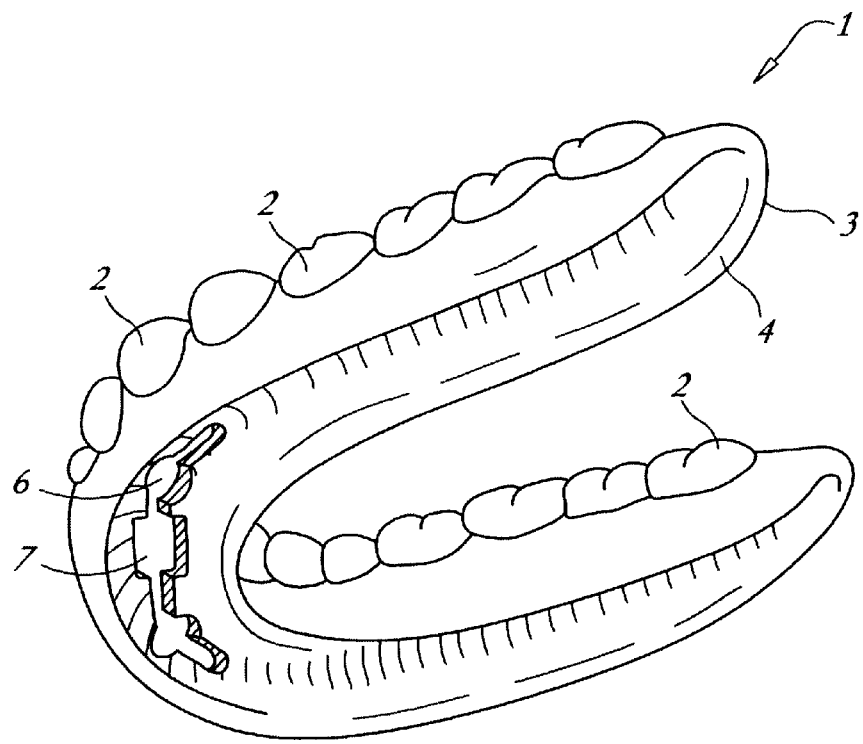
FIG. 4.) A perspective partial cutaway view of the invention showing the depressions created in the underside of the denture to accommodate both the securing device and the exposed portion of the implant.
Figure 4A:
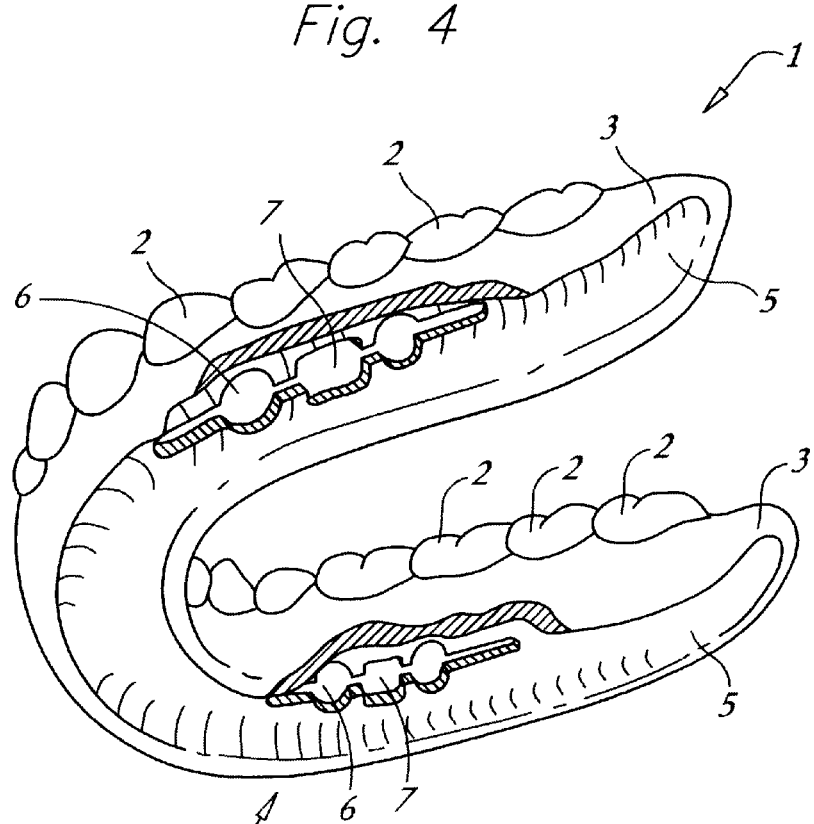
FIG. 4A.) A perspective partial cutaway view of the invention showing an alternate embodiment with multiple depressions created in the underside of the denture accommodating multiple securing devices and exposed portions of multiple implants.
Figure 5:
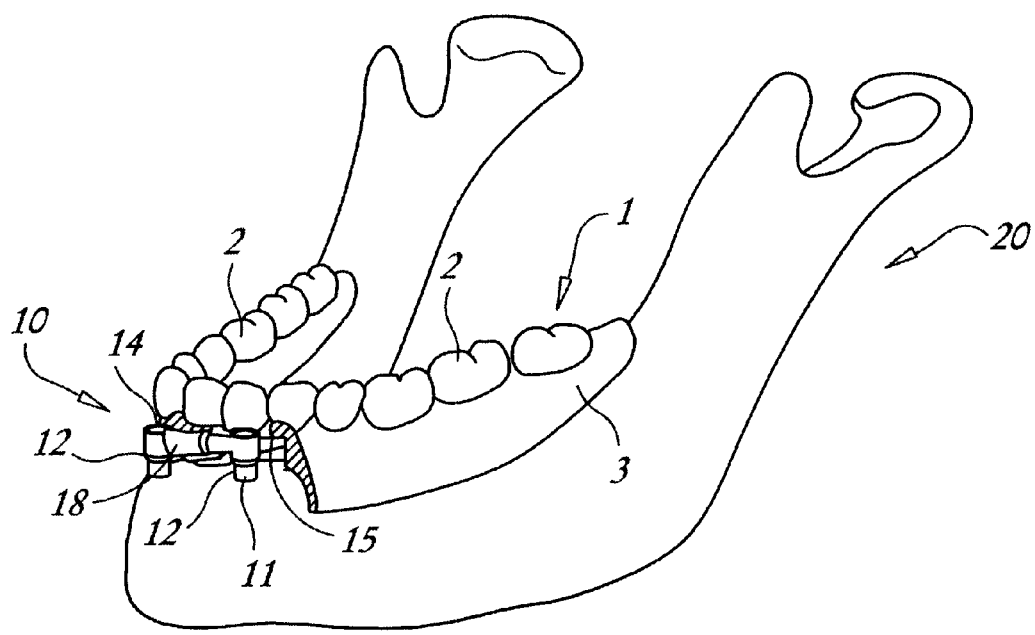
FIG. 5.) A perspective view of the invention showing the implant securing device secured to the denture.
Figure 5A:
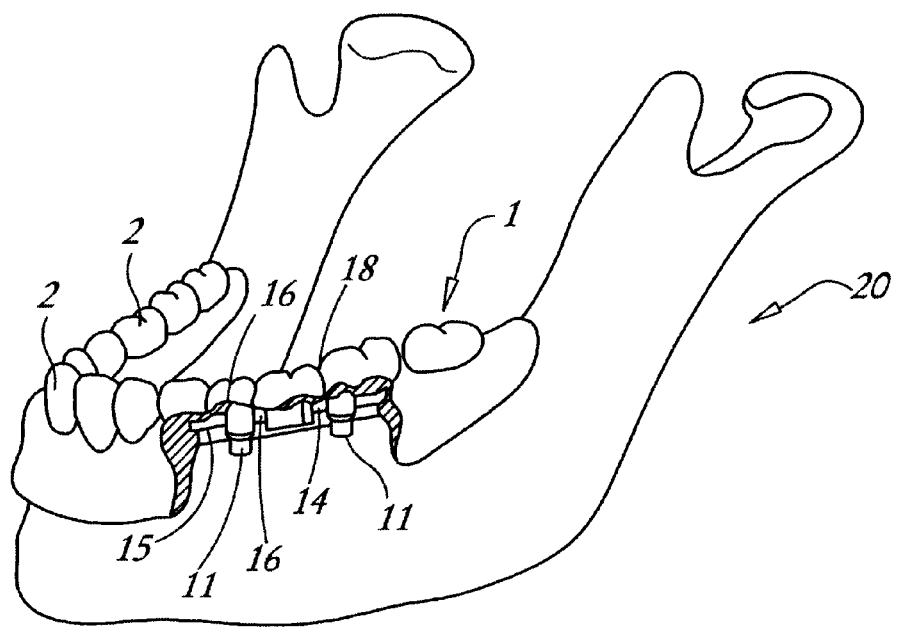
FIG. 5A.) A perspective partial cutaway view of the denture retrofitted with dental implant technology reversible attached to the dental implant.

The retrofitting of denture is shown generally in FIGS. 3, 4, and in FIGS. 3A, 4A, the respective multiple implant alternative embodiments, uses techniques well known to those versed in the art. First, denture base material is removed from the depression receptacle 5 of the denture base 3 to create the dental implant depression 6 so as to allow the denture 1 to accept protrusion of the exposed portion of the dental implant 10 including, but not limited to, the saddle bar 14 and caps 12. Sufficient material is removed so that the exposed portion of dental implants 10 can be snugly but not tightly accepted by dental implant depression 6.

Additional material is then removed from the dental implant depression 6 of the denture base 3 to create the securing device depression 7 for the receiving and attaching of the securing device 13 to the denture 1. Each implant 10 affixed to the denture wearer have at least one respective securing device 13 affixed to the denture 1. For dental implants 10 using a saddle bar 14, the securing device 13 is that often used is used is a C-clip 18. The C-clip 18 is made from resilient material such an appropriate plastic or metal;

has a C-shaped cross section; and has its length dependent upon the particular needs of the implant application. The alternate embodiment for the securing device 13 can include using the male-female O-ring snap attachment device.

The respective portions of the securing devices 13 are attached to securing device depression 7 using standard dental acrylic adhesive. The use of acrylic adhesive allows the attachment of the securing device 13 to be semi-permanent so that worn out securing devices can be readily replaced.

The denture 1 is then fitted to the denture wearer with further modifications are required using by the standard dental techniques for fitting dentures to ensure the that securing device(s) 13 can properly reversible engage the implant 10; that the denture 1 can properly accommodates the protrusion of the implant 10; and that the denture 1 is securely and comfortable fits the denture wearer.

Usually, the retrofitting of the denture can be accomplished in one office visit after the implant 10 has been affixed to the denture wearer. In this manner, the retrofitting of the denture with implant technology, saves the considerable cost of new denture specifically made for attachment of implant affixed to the denture wearer, saves office visit (usually two visits to create and fit the new denture) and dental laboratory time (usually takes at least week turn around time for denture creation). After being fitted with the implant, all is needed is a short office visit to retrofit the old dentures, and the patient is on her or his way.

The communicating to denture wearers of the benefits (snap on and off attachment, greater security, better fit, savings of time and expense) that can be obtained with the above described retrofitting of dentures with dental implant technology securing device can be used to overcome the natural reticence of the denture wearers to being fitted with dental implants and embracing dental implantology. In the preferred embodiment, this communication of benefits would occur through the dissemination delivered as advertisement through the mass media which would include but not be limited to wireless, print, direct mail solicitation, phone solicitation and Internet communication streams.

In the preferred embodiment, the dissemination would comprise of the information that would include bring to the attention of the denture wearer's the realization that they might have problems with their dentures. These problems would pertain to the securing the denture to the denture wearer when using traditional non-dental implant securing methods such as adhesive and the alike. Examples could be dramatically convened to the denture wearers of situations where the dentures failed to remain secured to the denture wearer in public and embarrassing situations. The examples could also include scenarios where the denture used to fit the denture wearer, but through the passage of time it no longer does.

After using this information to attract the attention of the denture wearer, follow-up information would then be given to the denture wearer of the new securing means for dentures that is now available to them. This follow up information would emphasize issues such that: the new securing means was now available would provide a superior attachment for dentures in comparison to the older traditional attachment methods, that attachment would be snap on/snap off; that the fit of denture to denture wearer would be better than using older attachment methods, that dentures that did not fit the denture wear as well as they used to can against fit as securing when the denture wearer first acquired them, that the new method provides for great savings in time and expense over the current dental practices for denture securing methods. The denture wearer would then be given contact information to obtain the retrofitting services.

In the preferred embodiment, the communication of the benefits of retrofitting dentures to overcome reticence of dental implantology would include the marketing that used servicenames and tradenames to identify the invention as it is being used. The servicenames in the preferred embodiment would include "CLIP TIGHT FEEL RIGHT" and "CLIP TIGHT FIT RIGHT" to identify the method for retrofitting dentures with dental implant technology. The tradename that would be used to identified retrofitted dentures "CLIP-TIGHT DENTURES"

The foregoing is considered illustrative of the principles and general intent of the invention. As numerous alterations, modifications and changes will easily occurred with those skilled in the art, the foregoing is not to act as a limitation upon the invention as to its exact construction and operation shown and described, accordingly, all suitable and appropriate modifications and equivalents may be resorted to that arise within the scope of the patent.

I claim:

1. A method of modifying a denture, the denture being reversibly secured to a denture wearer using a non-dental implant securing device, the denture comprising of teeth embedded into a denture base which forms a receptacle depression, wherein the modification comprises of:

A) enlarging of the said receptacle depression to accept at least a portion of at least one dental implant securing device and to accept at least a portion of at least one denture implant affixed to the denture wearer, and B) attaching of at least one dental implant securing device to said denture.

2. A method of modifying a denture as set forth in claim 1 wherein the attaching of the dental implant securing device, positions the dental implant securing device to reversibly attach to a portion of the dental implant affixed to a denture wearer.

3. A method of modifying a denture as set forth in claim 1 wherein the dental implant securing device is attached to the depression receptacle of the denture.

4. A method of modifying a denture as set forth in claim 1 wherein the dental implant securing device is attached by acrylic adhesive.

5. A method of modifying a denture as set forth in claim 1 wherein the denture is a partial denture.

6. A method of modifying a denture as set forth in claim 1 wherein the denture is a full denture.

7. A method of modifying a denture as set forth in claim 1 wherein the securing device is a clip with a C-shaped cross section.

8. A method of modifying a denture as set forth in claim 7 wherein the clip is made of resilient material.

9. A method of modifying a denture as set forth in claim 1 wherein the enlarging of the depression creates an additional depression to accommodate the securing device.

* * * * *